United States Patent [19]

Strianse et al.

[11] 4,362,715

[45] Dec. 7, 1982

[54] COSMETIC VEHICLE

[75] Inventors: Sabbat J. Strianse, Caldwell; Howard S. Sherry, Cherry Hill, both of N.J.; Elliot P. Hertzenberg, Wilmington, Del.

[73] Assignee: PQ Corporation, Valley Forge, Pa.

[21] Appl. No.: 213,262

[22] Filed: Dec. 5, 1980

Related U.S. Application Data

[63] Continuation-in-part of Ser. No. 145,514, May 1, 1980, abandoned.

[51] Int. Cl.$^3$ .................... A61K 7/02; A61K 7/32; A61K 7/48; A61K 9/06; A61K 31/74; A61K 31/78; A61K 47/00
[52] U.S. Cl. ........................... 424/78; 424/63; 424/65; 424/69; 424/81; 424/357; 424/358
[58] Field of Search ............... 424/63, 65, 69, 78, 424/79, 81, 357, 358

[56] References Cited

U.S. PATENT DOCUMENTS

| | | | |
|---|---|---|---|
| 2,882,234 | 4/1959 | Gorter | 252/62.51 |
| 3,012,853 | 12/1961 | Milton | 252/453 X |
| 3,130,007 | 4/1964 | Rabo | 252/453 X |
| 3,329,628 | 7/1967 | Gladrow | 252/453 |

OTHER PUBLICATIONS

Carbopol, Supplement No. 3, Jul. 1959 to "Carbopol 934" Bulletin, B.F. Goodrich Chem. Co., Cleveland, Ohio, 3 pp.
Harry, The Principles & Practice of Mod Cos, Cos. Materials, vol. 2, Leonard Hill Ltd., London, 1950, pp. 182, 183.
Bennett, The Cos. Formulary, Chem. Pub. Co., NY, vol. XVI, 1971, pp. 124, 125.

*Primary Examiner*—Anna P. Fagelson
*Attorney, Agent, or Firm*—Ernest G. Posner; J. S. Stephen Bobb; F. C. Philpitt

[57] ABSTRACT

A combination of an acidic functional polymer and zeolite and/or amorphous alumino silicate provides a gel suitable as a cosmetic vehicle plus supplying functionality as well. The components combine easily to provide a creamy gel that is compounded with other ingredients to provide the complete cosmetic composition. The zeolite or amorphous alumino silicate is present in a sufficient quantity to provide functionality as well as the desired rheology. The combination can be used to compound astringent creams or lotions, make-up bases, facial masks, deodorant compositions, antiperspirants, anti-acne compositions, wrinkle smoothers or erasers, pore minimizers, and body lotions. An especially useful zeolite or amorphous alumino silicate is a material that contains aluminum as the cation.

13 Claims, No Drawings

COSMETIC VEHICLE

This application is a continuation-in-part of our copending application Ser. No. 145,514, filed May 1, 1980, abandoned.

BACKGROUND OF THE INVENTION

This invention relates to the formulation of cosmetic compositions. In particular the invention provides a vehicle for various cosmetic compositions that is functional in addition to its pseudoplastic character, which makes it useful as a bodying agent. This vehicle comprises a combination of an organic polymer of acidic functionality and a zeolite or a combination of zeolites. Zeolite precursor gels are also useful.

Two of the important considerations in compounding cosmetic compositions are ease of application and the feel of the cosmetic on the skin. In general, it is felt that pseudoplastic character and thixotropy are desirable attributes in compounding such materials. Some of the materials used to provide the desired properties include celluloses, xanthan gums, natural gums, soaps and some surface active agents. VEEGUM ®, a magnesium aluminum silicate clay of the smectite series (VEEGUM is a registered trademark of R. T. Vanderbilt Co.) is often used to provide the pseudoplastic properties. This material acts by hydration due to an expanding lattice structure. In general, these prior art materials provide their viscosity alteration at very low concentration, and they have no further functional role in the cosmetic composition.

SUMMARY OF THE INVENTION

We have discovered a unique combination of materials that provides the desired rheology for the cosmetic composition and provides cosmetic functionality as well. This combination comprises acidic polymers and a zeolite and/or amorphous form of alumino silicate. The polymer of acid functionality and the zeolite interact to provide a creamy gel which can be compounded with various other ingredients to provide the complete cosmetic composition. The zeolite or other alumino silicate is present in sufficient quantity that the creamy gel provides functionality as well as the described rheology. The creamy gel can be used to compound astringent creams or lotions, makeup bases, facial masks, deodorant compositions, antiperspirants, anti-acne compositions, wrinkle smoothers or erasers, pore minimizers, and body lotions.

THE INVENTION

The zeolites that are important ingredients of the composition of our invention can be naturally occurring and/or synthetic crystalline metal alumino silicates. The chemical composition, structure, preparation, and physical and chemical properties of zeolites have been disclosed and discussed in numerous articles and texts. These sources include D. W. Breck's book, *Zeolite Molecular Sieves; Structure, Chemistry and Uses* (Wiley-Interscience: 1974). Synthetic zeolites are preferred for the compositions of our invention because they can be specially manufactured to provide the desired properties. Synthetic crystalline metal alumino silicates such as those described in U.S. Pat. Nos. 2,882,243-4; 3,012,853; 3,130,007 and 3,329,628, among others, are suitable as ingredients in our composition.

Such zeolites are prepared by combining aqueous solutions containing sources of silica, alumina and alkali to produce an alkaline alumino-silicate gel which crystallizes upon hydro-thermal treatment. Washing and drying steps complete the preparation. The intermediate alumino-silicate gel can also be used as an ingredient in our composition. The gel can be used as it is produced after washing, or it can be substantially dewatered.

Both the zeolite and the alumino-silicate gel are usually prepared in the sodium form. These materials can be used in this form, or ion exchanged thereby substituting a preferred metal for the sodium. Useful zeolites and gels conform to the formula:

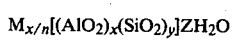
$$M_{x/n}[(AlO_2)_x(SiO_2)_y]ZH_2O$$

In this formula x and y are integers greater than 6, the molar ratio of x to y is 0.1 to 1.1, Z varies from 8 to 250, and M is a metal with the valence of n. Zeolite A and its precursor gel wherein x and y are 12 and Z is about 20 to 40 are useful. Zeolites X and Y, which are more siliceous, and their precursor gels are also useful. Other variations of such zeolites can be useful, such as acid-washed or silane-treated materials.

Zeolites or alumino-silicate gels that have aluminum in the cationic form, $Al^{+3}$, are of particular advantage in the composition of our invention since the aluminum cation has certain interactions with the skin providing cosmetic functionality. Only those zeolites that can accommodate the $Al^{+3}$ ion within the crystal lattice (the so-called cages) are useful in such applications. Usually the more siliceous zeolites such as Zeolite Y are useful in such applications. Zeolite NaY that has been exchanged using an aluminum chloride or equivalent solution are useful in our compositions. Other more siliceous natural and synthetic zeolites are also useful when ion exchanged to yield $Al^{+3}$ loaded zeolite.

The other ingredient of our cosmetic vehicle is any of a number of high molecular weight polymers of acidic functionality that will interact with zeolites and/or aluminosilicate gels to form a creamy gel with pseudoplastic viscosity behavior. Carboxy vinyl polymer with active carboxyl groups is especially useful for these compositions.

The functional cosmetic vehicle of our invention has the following composition:

Zeolite or alumino-silicate gel: 5 to 25%
Acidic polymer: 0.1 to 10%
Water: balance to 100%

We prefer the concentration of the polymer to be 0.2 to 3.5%. The vehicle is prepared as follows. A portion of the water is heated to 50°–90° C. and stirred vigorously. The polymer is added slowly. Stirring continues until a homogeneous solution forms. The zeolite and/or gel is dispersed in the remainder of the water. This dispersion is combined with the acidic polymer solution. Stirring continues until a gel forms. The product is a creamy translucent gel with the desired smooth effect on the skin. The pH varies from about 5.5 to 8.5.

This gel by itself has numerous cosmetic functions. It has an astringent effect on the skin, thereby contributing to the necessary actions required for makeup bases, facial masks, wrinkle smoothers or erasers, pore minimizers, deodorants and antiperspirants. The amorphous materials and especially the zeolites are effective adsorbents so that our vehicle is effective for cleansing creams and anti-acne creams.

The vehicle of our invention can constitute 10 to 80% by weight of the cosmetic composition. The remaining ingredients can provide additional cosmetic and/or formulation functionality. Such additional ingredients can include pigments, perfumes, odorants, carboxy methyl cellulose, alcohols of various types, various powders such as talc, hydrophobic materials such as silane-treated silica, various glycols, various surfactants, sodium stearates, various silica gels, clays and the like. More specific formulations are identified in the examples. While our vehicle is a creamy gel, and lotions and creams constitute the most common finished compositions realized therefrom, stick type formulations are also possible.

The vehicle of our invention and the products derived from it are stable products which are easily handled and stored. The properties of the vehicle are easily adjusted to the ranges generally recognized as safe for application to human skin.

EXAMPLES

The following examples illustrate certain embodiments of our invention. They are not presented to establish the scope of our invention which is fully recited in the specification and the claims. All proportions are in parts by weight (pbw) or percent by weight (%) unless otherwise indicated.

EXAMPLE 1

This example illustrates the preparation of a cosmetic vehicle according to the concepts of our invention. Water (98 pbw) was heated to about 80° C. and agitated using a homogenizer-mixer; then 2 pbw of CARBOPOL ® was added slowly to the water. Stirring was continued until a homogeneous solution was obtained. (CARBOPOL is a registered trademark of the B. F. Goodrich Chemical Company.) CARBOPOL 941 is sometimes referred to as Carbomer 941, and is a carboxypolymethylene, carboxy vinyl polymer. An aluminosilicate gel precursor of Zeolite NaX with a loss on ignition of 40% (10 pbw) was dispersed in 70 pbw of water. The dispersion of the gel in water was then added to 20 pbw of the CARBOPOL solution with stirring which continued until a gel formed. The product was a heavy translucent gel with a pH of 7.70.

EXAMPLE 2

Zeolite NaX (10 pbw) was dispersed in 70 pbw of water and added to 20 pbw of the CARBOPOL solution described in Example 1. The zeolite had a loss on ignition of 18.6%. The process was carried out exactly as described in Example 1 and the product was an opaque gel with a pH of 7.40.

EXAMPLE 3

The zeolite described in Example 2 was used in the same process, but 15 pbw of the zeolite was dispersed in 65 pbw of water. The product was an opaque gel with a pH of 7.80.

EXAMPLE 4

The process of Example 2 was repeated except that Zeolite CaA (23% loss on ignition) was used. The product was an opaque gel with a pH of 6.40.

EXAMPLE 5

The process described in Example 4 was repeated except that 20 pbw of Zeolite CaA was dispersed in 60 pbw of water. The resulting gel was opaque and had a pH of 7.1.

EXAMPLE 6

The process described in Example 2 was repeated except that Zeolite NaA with a loss on ignition of 22% was used. The resulting gel had a pH of 8.4.

The products of Examples 1–6 were gels of varying pH and while they were cohesive, they could easily be spread on the skin, forming a smooth coating as required for a cosmetic vehicle.

EXAMPLE 7

A wrinkle smoother or eraser with the following formula was prepared:
Vehicle gel of Example 1: 10.0 pbw
CMC (carboxy methyl cellulose): 3.0 pbw
Propylene glycol: 1.0 pbw
Red pigment: 0.1 pbw
Water: to 100 pbw The vehicle and water were combined and heated to 60° C. and stirred; then the CMC was added slowly, followed by the propylene glycol. This mixture was colloid milled before the pigment was blended into the creamy material. The product had a pH of 8.5 and could be applied to the skin easily to form a smooth coating. As the coating dried and after drying a noticeable drawing and smoothing of the skin could be felt.

EXAMPLE 8

The process of preparing a wrinkle smoother described in Example 7 was repeated except that the vehicle described in Example 2 was used. The results were similar.

EXAMPLE 9

A de-oiling acne cream with the following formula was prepared using the gel prepared as described in Example 1.
Vehicle gel of Example 1: 40.0 pbw
CMC: 2.0 pbw
ZnO: 5.0 pbw
$TiO_2$: 2.0 pbw
Talc: 3.0 pbw
QUSO ® WR-50 hydrophobic silica: 0.5 pbw
Red, yellow, brown pigments: 0.8 pbw
Propylene glycol: 2.0 pbw
PROCETYL ® AWS propoxylated ethoxylated cetyl alcohol: 4.0 pbw
Alcohol SD40: 20.0 pbw
Water: to 100.0 pbw QUSO is a registered trademark of PQ Corporation.
PROCETYL is a registered trademark of Corda Inc.

The water was heated to 60° C. and stirred. The vehicle gel was added, followed by the CMC. A blend of the remaining powdered materials was added. Stirring was continued until the material was homogeneous. The propylene glycol and PROCETYL AWS were added before cooling to 40° C. and addition of the alcohol. The mixture passed through the colloid mill twice. The cream had a pH of 8.7.

EXAMPLE 10

A second de-oiling cream was prepared as described in Example 9, except that the vehicle gel described in Example 4 was used. The cream had a pH of 7.7.

EXAMPLE 11

A de-oiling pore minimizing cream with the following formula was prepared with the vehicle prepared as described in Example 3:

Vehicle of Example 3: 35.0 pbw
ZnO: 5.0 pbw
Talc: 3.0 pbw
TiO$_2$: 2.0 pbw
QUSO ® WR-50: 1.0 pbw
Red, yellow, brown pigments: 0.8 pbw
Propylene glycol: 2.0 pbw
PROCETYL ® AWS: 3.0 pbw
Alcohol SD40: 20.0 pbw
Water: to 100.0 pbw Heat the water to 60° C. and add the vehicle gel with stirring. Add the propylene glycol and PROCETYL AWS. Blend the powdered ingredients and add slowly. Stir until uniform and cool before passing through the colloid mill twice. A thin lotion that had a pH of 8.9 resulted. An astringent effect was noted when the lotion dried on the skin.

EXAMPLE 12

A second pore minimizing cream was prepared as described in Example 11 except that the vehicle of Example 1 was used. The pH of the product was 8.85 and a distinct astringent effect was noted when the lotion dried on the skin.

EXAMPLE 13

A body astringent and freshener with the following formula was prepared with the vehicle prepared as described in Example 4.

Vehicle of Example 4: 8.00 pbw
Propylene glycol: 3.00 pbw
Alcohol SD40: 30.00 pbw
PROCETYL ® AWS: 5.00 pbw
QUSO ® WR-50: 1.00 pbw
Triethanolamine: 0.06 pbw
SEQUESTRENE ® Na$_2$ (disodium EDTA): 0.05 pbw
Water: to 100.00 pbw
SEQUESTRENE is a registered trademark of Ciba-Geigy Inc.

Disperse the QUSO in the propylene glycol. Mix procetyl AWS, water, the vehicle and SEQUESTRENE Na$_2$. Add the QUSO dispersion to the mixture and add the triethanolamine. Stir until thoroughly mixed and then homogenize. The pH of the liquid was 6.2, and the liquid had a freshening feeling on the skin.

EXAMPLE 14

A deodorant lotion with the following formula was prepared using the vehicle prepared as described in Example 6.

| | | |
|---|---|---|
| A { | Isopropyl myristate | 10.00 pbw |
| | TWEEN ® 80 | 4.20 pbw |
| | ARLACEL ® 80 | 1.00 pbw |
| B { | Propylene glycol | 5.00 pbw |
| | IRGASAN ® DP-300 | 0.10 pbw |
| | Water | 45.70 pbw |
| C { | Vehicle of Example 6 | 20.00 pbw |
| | Water | 14.00 pbw |

A and B are heated separately to 75° C. Add A to B with stirring to form an emulsion. Cool to 60° C. and add C slowly to form a gel before cooling to 50° C. and homogenizing. The heavy lotion has a pH of 8.6.

TWEEN is a registered trademark of ICI United States Inc. for a mixture of oleate esters of sorbitol and sorbitol anhydrides.

ARLACEL is a registered trademark of ICI United States Inc. for sorbitan oleate.

IRGASAN is a registered trademark of Ciba-Geigy Corp. for 5 Chloro-2-(2,4-Dichlorophenoxy)phenol.

EXAMPLE 15

The preparation of the cosmetic vehicle of Example 1 is repeated except that CARBOPOL ® 934 or 940 replaced the CARBOPOL ® 941. Gels form that are useful in the formulations of the examples.

We claim:

1. A cosmetic vehicle comprising a carboxyvinyl polymer with active carboxyl groups and a zeolite having the formula:

$$M_{x/n}[(AlO_2)_x(SiO_2)_y]zH_2O$$
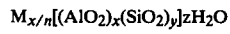

wherein x and y are integers greater than 6, the molar ratio of x to y is 0.1 to 1.1, z varies from 8 to 250 and M is a metal of valence n, said polymer-zeolite composition being a creamy gel with a pseudoplastic viscosity and having a pH of 5.5 to 8.5.

2. The cosmetic vehicle of claim 1 consisting of 0.1 to 10% by weight of the acidic polymer, 5 to 25% by weight of the zeolite and the balance to 100% by weight of water.

3. The composition of claims 1 or 2 wherein the zeolite is Zeolite A, Zeolite X or Zeolite Y.

4. The composition of claim 3 wherein M is aluminum in the cationic state.

5. The composition of claim 3 wherein the zeolite is Zeolite AlY.

6. A cosmetic vehicle comprising 0.1 to 10% by weight of a high-molecular-weight organic polymer with active carboxyl groups and 5 to 25% by weight of a crystalline zeolite, and the balance to 100% by weight of water, said polymer-zeolite combination being a creamy gel with a pseudoplastic viscosity and having a pH of 5.5 to 8.5, said zeolite of the formula:

$$M_{x/n}[(AlO_2)_x(SiO_2)_y]ZH_2O$$
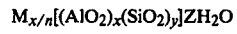

wherein x and y are integers greater than 6, the molar ratio of x to y is 0.1 to 1.1, Z varies from 8 to 250 and M is a metal of valence n.

7. The composition of claim 6 wherein the zeolite is Zeolite A, Zeolite X or Zeolite Y.

8. The composition of claim 6 wherein M is aluminum in the cationic state.

9. The composition of claim 6 wherein the zeolite is Zeolite AlY.

10. A cosmetic vehicle comprising a carboxyvinyl polymer with active carboxyl groups and a crystalline zeolite, said polymer-zeolite combination being a creamy gel with a pseudoplastic viscosity and having a pH of 5.5 to 8.5, said crystalline zeolite having the formula:

$$M_{x/n}[(AlO_2)_x(SiO_2)_y]ZH_2O$$
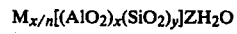

wherein x and y are integers greater than 6, the molar ratio of x to y is 0.1 to 1.1, z varies from 8 to 250 and M is a metal of valence n.

11. The composition of claim 10 wherein the zeolite is Zeolite A, Zeolite X or Zeolite Y.

12. The composition of claim 10 wherein M is aluminum in the cationic state.

13. The composition of claim 10 wherein the zeolite is Zeolite AlY.

* * * * *